United States Patent [19]

Houlihan

[11] 4,162,317
[45] Jul. 24, 1979

[54] SUCCINIC ACID ESTERS OF 2-HYDROXYBUTYL-4,5-DIHYDRO-3(2H)-PYRIDAZINONES AND THEIR USE AS MUSCLE RELAXANT AGENTS

[75] Inventor: William J. Houlihan, Mountain Lakes, N.J.

[73] Assignee: Sandoz, Inc., E. Hanover, N.J.

[21] Appl. No.: 909,516

[22] Filed: May 25, 1978

[51] Int. Cl.² ............... C07D 237/14; A61K 31/50
[52] U.S. Cl. .................................. 424/250; 544/239
[58] Field of Search .......................... 544/239; 424/250

[56] References Cited

U.S. PATENT DOCUMENTS 3,862,943  1/1975  Houlihan .......................... 544/239

Primary Examiner—Mark L. Berch
Attorney, Agent, or Firm—Gerald D. Sharkin; Robert S. Honor; Thomas O. McGovern

[57] ABSTRACT

Succinic acid esters of -4,5-dihydro-3(2H)-pyridazinones of the formula

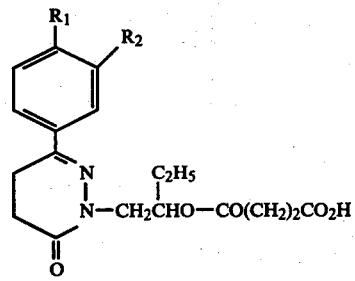

where
$R_1$ is hydrogen or halo having an atomic weight of from 19 to 36, and
$R_2$ is hydrogen, chloro or lower alkyl having 1 to 4 carbon atoms are useful as central nervous system depressants, in particular, as muscle relaxants.

4 Claims, No Drawings

SUCCINIC ACID ESTERS OF 2-HYDROXYBUTYL-4,5-DIHYDRO-3(2H)-PYRIDAZINONES AND THEIR USE AS MUSCLE RELAXANT AGENTS

This invention relates to succinic acid esters of 4,5-dihydro-3(2H)-pyridazinones. More particularly, it relates to succinic acid esters of (2-hydroxybutyl) and aryl substituted -4,5-dihydro-3(2H)-pyridazinones, to a method for their preparation and to their use in pharmaceutical compositions.

The compounds of this invention may be represented by the following formula:

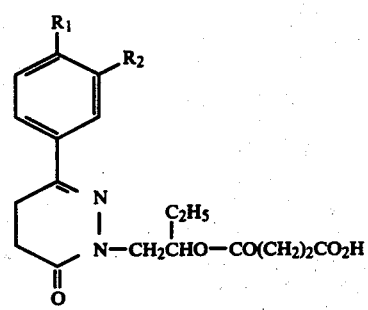

wherein
$R_1$ represents hydrogen or halo having an atomic weight of from about 19 to 36, and
$R_2$ represents hydrogen, chloro or methyl.

The compounds of formula (I) are prepared in accordance with the following process:

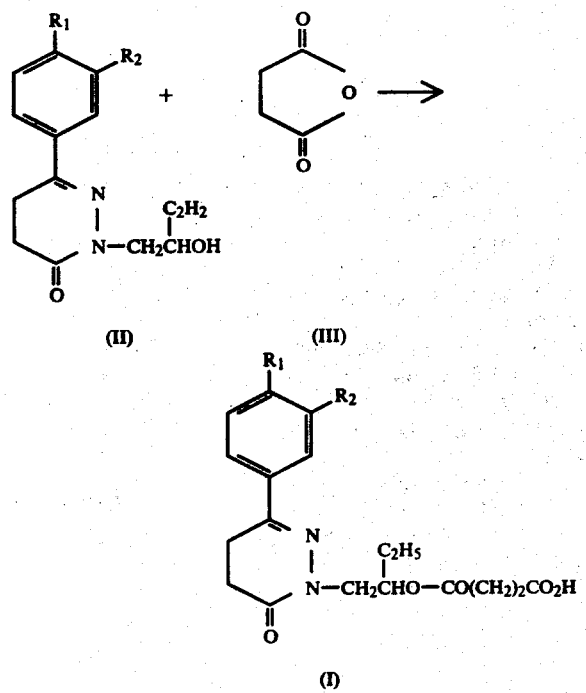

wherein $R_1$ and $R_2$ are as defined above.

The compounds of formula (I) are prepared by reacting a compound of formula (II) with succinic anhydride of formula (III). The reaction is preferably run in an inert solvent, in particular, pyridine, at temperatures of from about 50° to 125° C. for a period of from about 1 to 4 hours. The particular solvent, temperature or time at which the reaction is carried out is not critical. The compound of formula (I) is recovered by conventional techniques, e.g., evaporation and recrystallization.

The compounds of formula (II) are known and can be prepared by methods described in United States Patent 3,931,176. The compound of formula (III) is known and is described in the literature.

The compounds of formula (I) are useful because they possess pharmacological activity in animals, such as mammals. In particular, the compounds are useful as central nervous system depressants, especially as muscle relaxants, as indicated (1) by their ability to produce docility in behavior tests in mice according to the 30-word adjective check sheet system basically as described by Irwin, S. (Gordon Research Conference, Medicinal Chemistry 1959) and Chen (Symposium of Sedative and Hypnotic Drugs, Williams, and Wilkins, 1954) and (2) by the rotorod test with trained mice basically as described by Dunham and Miya (J. Am. Pharm. Assoc. 45; 208, 1957).

The compounds of formula (I) may be combined with a pharmaceutically acceptable carrier or adjuvant. They may be administered orally or parenterally. For the above uses, the dosage will vary depending upon the mode of administration utilized and the particular compound employed. However, in general, satisfactory results are obtained when the compounds are administered at a daily dosage of from about 1 milligram to 200 milligrams per kilogram of animal body weight. This daily dosage is preferably given in divided doses, e.g., 2 to 4 times a day, or in sustained release form. For most large mammals, the total daily dosage is from about 75 to 2000 milligrams, and dosage forms suitable for internal administration comprise from about 19 milligrams to about 1000 milligrams of the compound in admixture with a solid or liquid pharmaceutical carrier or diluent.

Tablets and capsules containing the ingredients indicated below may be prepared by conventional techniques and are useful as a muscle relaxant at a dose of one tablet or capsule 2 to 4 times a day.

| Ingredient | Weight tablet | capsule |
|---|---|---|
| 6-(p-chlorophenyl)-2-(2-hydroxybutyl)-4,5-dihydro-3(2H)-pyridazinone, succinic acid ester | 50 | 50 |
| tragacanth | 10 | — |
| lactose | 197.5 | 250 |
| corn starch | 25 | |
| talcum | 15 | |
| magnesium stearate | 2.5 | |
| Total | 300 mg. | 300 mg. |

The following pharmaceutical compositions are formulated with the indicated amount of active agent using conventional techniques. The injectable suspension and the oral liquid suspension represent formulations useful as unit doses, which may be administered as muscle relaxants. The injectable suspension is suitable for administration twice a day whereas the oral liquid suspension is suitably administered 2 to 4 times per day for this purpose.

| Ingredient | Weight Injectable | Oral Suspension |
|---|---|---|
| 6-(p-chlorophenyl)-2-(2-hydroxybutyl)-4,5-dihydropyridazin-(2H)-3-one, succinic acid ester | 50 | 50 |
| sodium carboxy methyl cellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g. Tween 80) U.S.P. | — | 5 |
| sorbitol solution, 70%, U.S.P. | — | 2,500 |
| buffer agent to adjust pH for desired stability | — | q.s. |
| water | for injection q.s. to 1 ml. | q.s. to 5 ml. |

EXAMPLE 1

6-(p-chlorophenyl)-2-(2-hydroxybutyl)-4,5-dihydro-3(2H)-pyridazin(2H)-one, Succinic Acid Ester A mixture of 25 grams (0.089 mol) of 2-(2-hydroxybutyl)-6-(p-chlorophenyl)-4,5-dihydro-3(2H)-pyridazinone, 25 grams (0.25 mol) of succinic anhydride and 50 milliliters of pyridine are stirred and heated at 90° for 2.5 hours. The mixture is poured into 100 milliliters of water and 100 milliliters of methylene chloride. The organic layer is separated and washed twice with 100 milliliters of water following which it is treated with anhydrous magnesium sulfate and activated charcoal, filtered through celite and concentrated under vacuum. The residue is dissolved in a mixture of ethanol methylene dichloride and concentrated to about 80 milliliters volume. The precipitate formed (11.4 grams of bis-[2-(2-hydroxy-butyl)-6-(p-chlorophenyl)-4,5-dihydro-3(2H)-pyridazinone] succinate; m.p. 142°) is removed by filtration. The remaining filtrate is concentrated to a syrup (17 grams) and dissolved in 100 milliliters of diethyl ether. The solution is added dropwise to an ice-coated solution of diethylether saturated with dry ammonia gas. The white solid formed is filtered off, washed with diethyl ether and dissolved in $CH_2Cl_2$. The solution is filtered and then treated with petroleum ether yielding 6.0 grams of [2-(2-hydroxybutyl)-6-(p-chlorophenyl)-4,5-dihydro-3(2H)-pyridazinone] succinic acid ester (m.p. 90°-93°)

The $ED_{50}$ of 6-(p-chlorophenyl)-2-(2-hydroxybutyl)-4,5-dihydro-3(2H)-pyridazinone in the rotorod test is 129.2 milligrams per kilogram of animal body weight; and the compound is useful as a muscle relaxant when administered at a dose of 50 milligrams 2 to 4 times a day.

When the above procedure is carried out using an equivalent amount of 2-(2-hydroxybutyl)-6-phenyl-4,5-dihydro-3(2H)-pyridazinone, 6-(p-fluorophenyl)-2-(2-hydroxybutyl)-4,5-dihydro-3(2H)-pyridazinone, 6-(3,4-dichlorophenyl)-2-(2-hydroxybutyl)4,5-dihydro-3(2H)-pyridazinone, or 6-(3-methyl-4-chlorophenyl)-2-(2-hydroxybutyl)-4,5-dihydro-3(2H)-pyridazinone in place of the 6-(p-chlorophenyl)-2-(2-hydroxybutyl)-4,5-dihydro-3(2H)-pyridazinone, there is obtained the corresponding succinic acid ester.

What is claimed is:

1. A compound of the formula

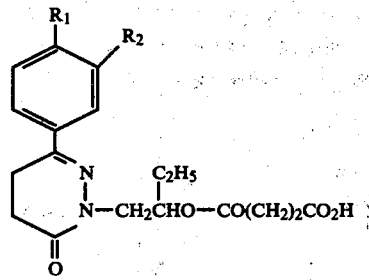

where $R_1$ is hydrogen fluoro or chloro, and
$R_2$ is hydrogen, chlorine or lower alkyl having 1 to 4 carbon atoms.

2. The compound of claim 1 which is 6-(p-chlorophenyl)-2-(2-hydroxybutyl)-4,5-dihydro-3(2H)-pyridazinone, succinic acid ester.

3. A pharmaceutical composition useful in the treatment of muscle tension consisting essentially of a therapeutically effective amount of a compound according to claim 1 and a pharmaceutically acceptable carrier therefore.

4. A method of treating muscle tension which comprises administering a therapeutically effective amount of a composition according to claim 3 to an animal in need of said treatment.

* * * * *